US00PP28463P2

(12) United States Plant Patent
Delabroye

(10) Patent No.: US PP28,463 P2
(45) Date of Patent: Sep. 26, 2017

(54) ***HEUCHERA* PLANT NAMED 'GUACAMOLE'**

(50) Latin Name: ***Heuchera* hybrid**
Varietal Denomination: Guacamole

(71) Applicant: Thierry Delabroye, Hantay (FR)

(72) Inventor: Thierry Delabroye, Hantay (FR)

(73) Assignee: SANDRINE DELABROYE, Hantay (FR)

( * ) Notice: Subject to any disclaimer, the term of this patent is extended or adjusted under 35 U.S.C. 154(b) by 44 days.

(21) Appl. No.: 14/998,521

(22) Filed: Jan. 15, 2016

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — Penny J. Aguirre

(57) ABSTRACT

A new cultivar of hybrid *Heuchera* named 'Guacamole', characterized by its leaves that are large in size, its strong growth habit, its late blooming period, its higher sun tolerance than is typical of *Heuchera* cultivars with light colored foliage, and its resistance to powdery mildew.

2 Drawing Sheets

Botanical classification: *Heuchera* hybrid.
Cultivar designation: 'Guacamole'.

BACKGROUND OF THE INVENTION

The present invention relates to a new and distinct cultivar of *Heuchera* of hybrid origin, botanically known as a *Heuchera* and is hereinafter referred to by its cultivar name 'Guacamole'.

The new cultivar arose from an ongoing breeding program conducted by the Inventor at his nursery in Hantay, France. The objectives of breeding program were to select cultivars that were strong growing with *Heuchera*×*villosa*-like properties with large leaves. The new cultivar was discovered as a chance seedling in a trial plot in April of 2014. The trial plot contained hundreds of cultivars and proprietary seedlings of *Heuchera* from the Inventor's breeding program. The parentage of 'Guacamole' is therefore unknown.

Asexual propagation of the new cultivar was first accomplished under the direction of the Inventor by in vitro propagation of meristem tissue in Rijswijk, The Netherlands in May of 2015. Asexual propagation of the new cultivar by stem cuttings and in vitro propagation has shown that the unique features are stable and reproduced true to type in successive generations.

SUMMARY OF THE INVENTION

The following traits have been repeatedly observed and represent the characteristics of the new cultivar. These attributes in combination distinguish 'Guacamole' as a new and unique cultivar of *Heuchera*.

1. 'Guacamole' exhibits leaves that are large in size.
2. 'Guacamole' exhibits a strong growth habit.
3. 'Guacamole' exhibits leaves that are light yellow-green in color.
4. 'Guacamole' exhibits a late blooming period.
5. 'Guacamole' exhibits higher sun tolerance than is typical of Heuchera cultivars with light colored foliage.

6. 'Guacamole' exhibits resistance to powdery mildew.

'Guacamole' can be most closely compared to the *Heuchera* cultivars 'Pistache' (U.S. Plant Pat. No. 19,585) and 'Bronze Beauty' (not patented). 'Pistache' differs from 'Guacamole' in having leaves that are smaller in size, in having a smaller plant size and in having less resistance to powdery mildew. 'Bronze Beauty' is similar to 'Guacamole' in leaf size and blooming period. 'Bronze Beauty' differs from 'Guacamole' in having leaves that are darker in color.

BRIEF DESCRIPTION OF THE DRAWINGS

The accompanying colored photograph illustrates the overall appearance and distinct characteristics of the new *Heuchera*.

The photograph in FIG. 1 was taken of a plant about 8-months (with overwintering) in age as grown outdoors in a 2-gallon container planted with 3 72-cell plugs in Deerfield, Mass. The photograph in FIG. 1 provides a side view of a plant of 'Guacamole'.

Figure 1:
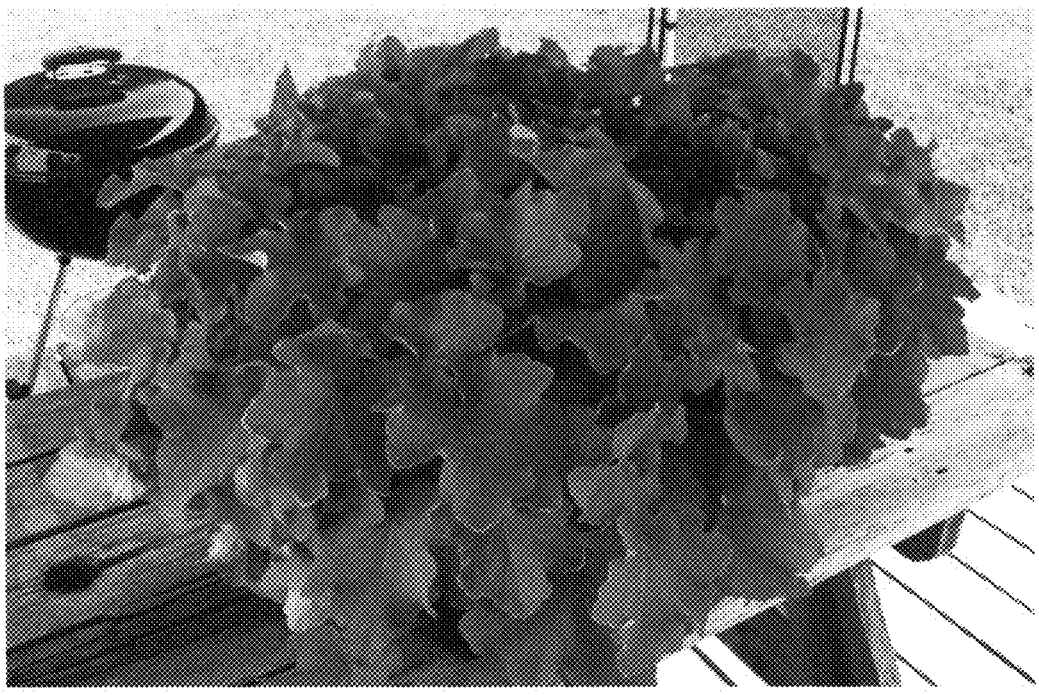
Figure 2:
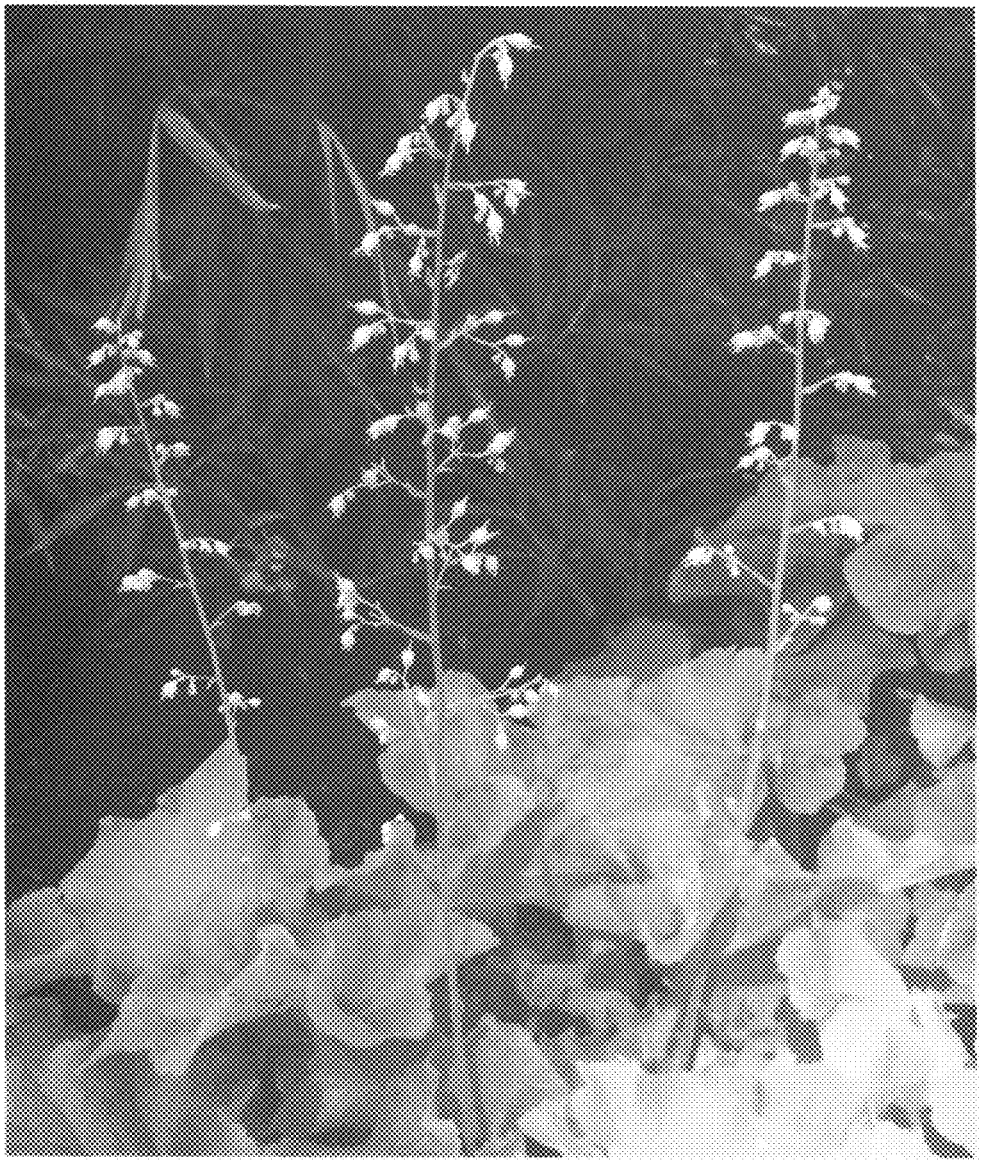

The photograph in FIG. 2 was taken of a 18 month-old plant as grown in a garden in New Hope, Minn. and provides a view of the inflorescences and the foliage color when grown in partial shade.

The colors in the photograph are as close as possible with the digital photography techniques available, the color values cited in the detailed botanical description accurately describe the colors of the new *Heuchera*.

DETAILED BOTANICAL DESCRIPTION OF THE PLANT

The following is a detailed description of plants six months in age as grown outdoors in a 2-gallon container (planted with 3 4-inch pots) in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General description:

*Blooming period*.—Average of 4 weeks in later spring and early summer in France (late blooming).

*Plant type*.—Herbaceous perennial.

*Plant habit*.—Compact, clump-forming, mounded foliage.

*Height and spread*.—An average of 20 cm in height from soil to top of leaves and 30 cm in width and an average of 60 cm (in bloom) and 70 cm in width in the landscape.

*Hardiness*.—At least in U.S.D.A. Zones 3 to 9.

*Diseases*.—Has shown resistance to powdery mildew caused by *Sphaerotheca pannosa*.

*Environmental stresses*.—Tolerant to heat and humidity and shown to have a high degree of sun tolerance.

*Root description*.—Fibrous roots, 164B in color.

*Brunching habit*.—flowering stem emerge from basal rosettes, no lateral branches.

*Propagation*.—In vitro propagation is the preferred method, stem cuttings and division are also possible.

*Growth rate*.—Vigorous.

Foliage description:

*Leaf shape*.—Orbicular.

*Leaf division*.—Simple.

*Leaf base*.—Cordate, overlapping.

*Leaf apex*.—Broadly acute (due to terminal lobe).

*Leaf venation*.—Laciniate, not conspicuous, vein color upper surface 144C and 144D, vein color lower surface 145D, main and secondary veins on lower surface are moderately covered with short hairs 1 mm in length and NN155D in color.

*Leaf margins*.—Lobed with average of 5 lobes per leaf, lobe margins bi-crenate with very small mucronate tips and hairy with hairs about 0.4 mm in length and NN155D in color.

*Leaf attachment*.—Petiolate.

*Leaf arrangement*.—Alternate, basal rosettes.

*Leaf orientation*.—Typically nearly horizontal to petiole and slightly wavy.

*Leaf surface*.—Upper surface very dull and primarily glabrous (just a few sparse hairs), lower surface dull with very finely puberulence.

*Leaf color*.—Young and mature upper surface; a blend of 144B and 144C, young and mature lower surface; 147D.

*Leaf size*.—Up to 10 cm in length and 12 cm in width.

*Leaf quantity*.—Average of 14 per basal rosette.

*Petioles*.—An average of 2 mm in diameter and 13 cm in length, color on newly emerging leaves 183C, color on mature leaves a blend of 144A to 144D and suffused near base with 183A, moderately strong, average angle of 80° to horizontal (0°=horizontal), surface is densely covered with short hairs; an average of 2 mm in length and NN155D in color.

*Bracts*.—None present.

Flower description:

*Inflorescence type*.—Numerous small bell-shaped flowers arranged on pyramidal panicles on flower scapes emerging from the base of the rosette.

*Inflorescence size*.—An average of 1 cm in height and 1 cm in width.

*Inflorescence number*.—An average of 3 per plant one year in age planted in the landscape.

*Flower fragrance*.—None.

*Flower quantity*.—Average of 86 flowers per inflorescence.

*Flower lastingness*.—Average of one week.

*Flower buds*.—Oblong to round in shape, an average of 2 mm in diameter and depth, 145A to 145B in color, surface is pubescent.

*Flower aspect*.—Multiple angles, upward, outward, drooping.

*Flower type*.—Campanulate.

*Flower size*.—About 6 mm in length and 4 mm in diameter.

*Petals*.—5, rotate arrangement and implanted in the hypanthium at base, narrow, lanceolate in shape, about 4 mm in length and 0.5 mm in width, margin is entire, apex is acute and curled downward, fused base, both surfaces are shiny and glabrous, immature and mature upper and lower surfaces NN155C in color.

*Calyx*.—Campanulate, sepals fused to hypanthium, 2 mm in depth and 3 mm in diameter.

*Sepals*.—5, fused, campanulate hypanthium, triangular in shape, 2 mm in length and 2 mm in width, margin is entire, apex is acute, truncate base, inner surface is glossy and smooth, outer surface is densely covered with pubescent hairs up to 5 mm in length and matched surface color, inner and outer surface color; 145B.

*Bracts*.—1, at base of petioles and peduncle, lanceolate in shape, 178A in color, up to 1 cm in length and 1 mm in width, acute apex, base truncate.

*Peduncles*.—Average of 1 cm in length, 1 mm in diameter, strong in strength, held upward to outward from flowering stem, 145A in color, slightly flushed at the base with 184A, surface is slightly glossy and densely covered with pubescent hairs, up to 1 mm in length and matches surface color.

*Pedicels*.—Average of 3 mm in length, 1 mm in diameter, moderately strong in strength, held upward to outward to drooping from the peduncle, 145A in color, slightly flushed at the base with 184A, surface is slightly glossy and densely covered with pubescent hairs, up to 1 mm in length and matches surface color.

Reproductive organs:

*Gynoecium*.—2 pistils, stigma is pointed in shape, NN155A in color, styles are 5 mm in length and NN155A in color, ovary is 1 mm in diameter, superior and 145A in color.

*Androcoecium*.—About 5 stamens, anthers are club-shaped, 0.5 mm in length and 170A in color, filament 3.5 mm in length and NN155A in color, pollen is minute in quantity and 170A in color.

*Seed/fruit*.—No fruit or seeds were observed.

It is claimed:

1. A new and distinct cultivar of hybrid *Heuchera* plant named 'Guacamole' as herein illustrated and described.

* * * * *